United States Patent
Herbst et al.

(10) Patent No.: US 10,662,399 B2
(45) Date of Patent: May 26, 2020

(54) AMYLASES

(71) Applicant: Henkel AG & CO. KGaA, Duesseldorf (DE)

(72) Inventors: Daniela Herbst, Duesseldorf (DE); Nina Mussmann, Willich (DE); Timothy O'Connell, Landsberg am Lech (DE); Claudia Lindner, Solingen (DE); Anna Krueger, Hamburg (DE); Neele Meyer-Heydecke, Handorf (DE); Garabed Antranikian, Seevetal-Hittfeld (DE); Anke Peters, Rosengarten (DE)

(73) Assignee: Henkel AG & Co. KGaA, Duesseldorf (DE)

(*) Notice: Subject to any disclaimer, the term of this patent is extended or adjusted under 35 U.S.C. 154(b) by 0 days.

(21) Appl. No.: 16/307,426

(22) PCT Filed: Jun. 1, 2017

(86) PCT No.: PCT/EP2017/063310
§ 371 (c)(1),
(2) Date: Dec. 5, 2018

(87) PCT Pub. No.: WO2017/211678
PCT Pub. Date: Dec. 14, 2017

(65) Prior Publication Data
US 2019/0153357 A1 May 23, 2019

(30) Foreign Application Priority Data
Jun. 6, 2016 (DE) ........................ 10 2016 209 880

(51) Int. Cl.
C12N 9/96 (2006.01)
C11D 3/386 (2006.01)
C12N 9/26 (2006.01)
C12N 15/70 (2006.01)

(52) U.S. Cl.
CPC ............ C11D 3/386 (2013.01); C12N 9/2414 (2013.01); C12N 15/70 (2013.01); C12Y 302/01001 (2013.01)

(58) Field of Classification Search
None
See application file for complete search history.

(56) References Cited

U.S. PATENT DOCUMENTS 10,100,299 B2 * 10/2018 Slupska ............... C12N 9/2425

FOREIGN PATENT DOCUMENTS

WO 2014164777 A1 10/2014

OTHER PUBLICATIONS

EPO, International Search Report and Written Opinion issued in International Application No. PCT/EP2017/063310, dated Aug. 1, 2017.
Database UniProt [Online]: XP055392492; Oct. 19, 2011.
Long-Liu Lin et al.: "Production and properties of a raw-starch-degrading amylase from the thermophilic and alkaliphilic *Bacillus* sp. TS-23", Biotechnology and Applied Biochemi, Academic Press, US; vol. 28, No. 1; Jan. 1, 1998; pp. 61-68; XP009111923.

* cited by examiner

*Primary Examiner* — Hope A Robinson
(74) *Attorney, Agent, or Firm* — Lorenz & Kopf, LLP

(57) ABSTRACT

The present disclosure relates to amylases which have an amino acid sequence that, over its entire length, shares at least about 70% sequence identity with the amino acid sequence of SEQ ID NO: 1, and to the production and use thereof. The amylases have a good cleaning performance.

13 Claims, No Drawings
Specification includes a Sequence Listing.

AMYLASES

CROSS-REFERENCE TO RELATED APPLICATION

This application is a U.S. National-Stage entry under 35 U.S.C. § 371 based on International Application No PCT/EP2017/063310, filed Jun. 1, 2017 which was published under PCT Article 21(2) and which claims priority to German Application No. 10 2016 209 880.2, filed Jun. 6, 2016, which are all hereby incorporated in their entirety by reference.

TECHNICAL FIELD

The present disclosure is within the field of enzyme technology. The present disclosure relates in particular to amylases and to the preparation thereof, to the amino acid sequence thereof that can be used in particular in respect of use in washing and cleaning agents, to all sufficiently similar amylases having an accordingly similar sequence according to SEQ ID NO:1 and to nucleic acids coding therefor. The present disclosure further relates to methods and to uses of said amylases and agents containing said amylases, in particular washing and cleaning agents.

BACKGROUND

Alpha-amylases are technically significant enzymes. The use of said amylases for washing and cleaning agents is well established in industry, and they may be found in modern, high-performance washing and cleaning agents. An alpha-amylase is an enzyme that catalyzes the hydrolysis of the inner α-(1-4) glycosidic bonds of the amylose, but not the cleavage of terminal or α-(1-6) glycosidic bonds. Alpha-amylases therefore represent a group of esterases (E.C. 3.2.1.1.). Alpha-amylases catalyze the cleavage of starch, glycogen and other oligo- and polysaccharides that have a α-(1-4) glycosidic bond. In this respect, alpha-amylases are active against starch residues in the laundry and catalyze the hydrolysis thereof (endohydrolysis). Alpha-amylases that have broad substrate spectra are used in particular when inhomogeneous raw materials or substrate mixtures need to be converted, i.e. for example in washing and cleaning agents, since dirt may consist of starch molecules and oligosaccharides having different structures. The alpha-amylases that are used in the washing or cleaning agents known from the prior art are usually of microbial origin and generally originate from bacteria or fungi, for example of the genera *Bacillus, Pseudomonas, Acinetobacter, Micrococcus, Humicola, Trichoderma* or *Trichosporon*. Alpha-amylases are usually produced in biotechnological processes known per se using suitable microorganisms, for example using transgenic expression hosts of the genus *Bacillus* or using filamentous fungi.

One particularly well-characterized alpha-amylase is an enzyme obtained from the alkalophilic *Bacillus* sp. strain TS-23, which hydrolyzes at least five types of starch (Lin et al., Biotechnol Appl Biochem, 28: 61-68, 1998). The alpha-amylase from *Bacillus* sp. strain TS-23 has a pH optimum of about 9, although it is stable over a wide pH range (i.e. from about 4.7 to about 10.8). Its optimal temperature is about 45° C., but the enzyme is also active at lower temperatures, for example from about 15 to about 20° C.

The U.S. Pat. Nos. 7,407,677 B2 and 8,852,912 B2 also disclose specific alpha-amylases and the fragments thereof for use in washing and cleaning agents.

Nevertheless, there is a need for (alpha) amylase variants that have altered biochemical properties and therefore provide improved performance in industrial applications.

BRIEF SUMMARY

This disclosure provides an amylase comprising an amino acid sequence which has at least about 70% sequence identity to the amino acid sequence given in SEQ ID NO:1 over the total length thereof.

This disclosure also provides an amylase obtained from the aforementioned amylase as a starting molecule by a single or multiple conservative amino acid substitutions; and/or as a starting molecule by fragmentation, deletion, insertion or substitution mutagenesis, wherein said amylase comprises an amino acid sequence which matches the starting molecule over a length of at least about 370 interconnected amino acids.

This disclosure further provides a method for preparing an amylase comprising the step of preparing a starting amylase which has at least about 70% sequence identity to the amino acid sequence given in SEQ ID NO:1 over the total length thereof.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it has now been found that an enzyme denoted as an alpha-amylase or a sufficiently similar amylase (based on the sequence identity) is particularly suitable for use in washing or cleaning agents, since it hydrolyzes a wide spectrum of starch substrates under standard washing conditions.

In a first aspect, the present disclosure therefore relates to an amylase comprising an amino acid sequence which has at least about 70% sequence identity to the amino acid sequence shown in SEQ ID NO:1 over the total length thereof.

The present disclosure therefore also relates to a method for preparing an amylase, comprising the preparation of a starting amylase which has at least about 70% sequence identity to the amino acid sequence shown in SEQ ID NO:1 over the total length thereof.

An amylase within the meaning of the present patent application therefore includes both the amylase per se and also an amylase prepared using a method as contemplated herein. All the information regarding the amylase therefore relates both to the amylase as a substance and to the corresponding methods, in particular methods for preparing the amylase, and the amylases prepared thereby.

The present disclosure further relates to the nucleic acids coding for the amylases as contemplated herein, to non-human host cells containing amylases as contemplated herein or nucleic acids as contemplated herein that code for said amylases, and to agents including amylases as contemplated herein, in particular washing and cleaning agents, washing and cleaning methods in which the amylases as contemplated herein are used, and to uses of the amylases as contemplated herein. A nucleotide sequence coding the amino acid sequence according to SEQ ID NO:1 is given in SEQ ID NO:2.

The present disclosure is based on the surprising finding that an amylase as contemplated herein that comprises an amino acid sequence that is at least about 70% identical to the amino acid sequence given in SEQ ID NO:1 causes the hydrolysis of a wide spectrum of starch substrates under standard washing conditions. This is in particular surprising to the extent that no amylases having comparable sequence homology have been described for use in cleaning agents until now.

The amylases as contemplated herein have high stability in washing or cleaning agents, for example against surfactants and/or bleaching agents and/or against the effects of temperature and/or against acidic or alkaline conditions and/or against pH changes and/or against denaturing or oxidizing agents and/or against proteolytic breakdown and/or against a change in the redox conditions. In particularly preferred embodiments of the present disclosure, amylase variants having improved performance are therefore provided. Such advantageous embodiments of amylases as contemplated herein therefore allow for improved washing results on starch-containing stains in a wide temperature range.

An amylase as contemplated herein has enzymatic activity, i.e. it is capable of hydrolyzing starch and oligosaccharides, in particular in a washing or cleaning agent. An alpha-amylase as contemplated herein is therefore an enzyme that catalyzes the hydrolysis of α-(1-4) glycosidic bonds in glycosidic substrates and is therefore capable of cleaving starch or oligosaccharides. Furthermore, an amylase as contemplated herein is preferably a mature alpha-amylase, i.e. the catalytically active molecule without signal peptide(s) and/or propeptide(s). Unless stated otherwise, the given sequences also relate to mature (processed) enzymes in each case.

In various embodiments of the present disclosure, the amylase comprises an amino acid sequence that is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5%, about 98.8%, about 99.0%, about 99.2%, about 99.4%, about 99.6% or about 99.8% identical to the amino acid sequence given in SEQ ID NO:1 over the total length thereof.

In other various embodiments of the present disclosure, the amylase is a free enzyme. This means that the amylase can directly interact with all the components of an agent and, if the agent is a liquid agent, that the amylase can be in direct contact with the solvent of the agent as contemplated herein (e.g. water). In other embodiments, in one agent, the amylase as contemplated herein may form a complex with other molecules or may comprise a "covering". Here, a single amylase molecule or a plurality of amylase molecules may be separated from the other components of an agent by a structure surrounding said molecule(s). By way of example, without being limited thereto, a separating structure of this type encloses vesicles, such as a micelle or a liposome. The surrounding structure may however also be a virus particle, a bacterial cell or a eukaryotic cell. In various embodiments, the amylase as contemplated herein may be contained in cells of *Bacillus*, which expresses this amylase, or in cell culture supernatants of such cells.

The identity of nucleic acid sequences or amino acid sequences is determined by sequence comparison. This sequence comparison is based on the established and commonly used BLAST algorithm (cf. for example Altschul, S. F., Gish, W., Miller, W., Myers, E. W. & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, p. 3389-3402) and takes place in principle by similar series of nucleotides or amino acids in the nucleic acid sequences or amino acid sequences being assigned to one another. The relevant positions being assigned in a table is referred to as alignment. Another algorithm available in the prior art is the FASTA algorithm. Sequence comparisons (alignments), in particular multiple sequence alignments, are created using computer programs. For example, the Clustal series (cf. for example Chenna et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-217) or programs based on these programs or algorithms are often used. Sequence comparisons (alignments) using the Vector NTI® Suite 10.3 computer program (Invitrogen Corporation, 1600 Faraday Avenue, Carlsbad, Calif., USA) comprising the predetermined standard parameters are also possible, the AlignX module of which is based on ClustalW for the sequence comparisons.

A comparison of this type also makes it possible to provide information regarding the similarity between the compared sequences. It is usually given in percentage identity, i.e. the proportion of identical nucleotides or amino acid residues in the same positions or in positions corresponding to another in an alignment. The broader term "homology" also takes preserved amino acid exchanges in amino acid sequences into account, i.e. amino acids having similar chemical activity, since they usually carry out similar chemical activity within the protein. Therefore, the similarity of the compared sequences may also be given in percentage homology or percentage similarity. Statements regarding identity and/or homology may be made for entire polypeptides or genes, or only for particular regions. Homologous or identical regions of different nucleic acid sequences or amino acid sequences are therefore defined in the sequences by matches. Such regions often have identical functions. They may be small and include only a few nucleotides or amino acids. Such small regions often have essential functions for the overall activity of the protein. It may therefore be useful for sequence matches to only relate to individual regions, which may be small. Unless stated otherwise, however, statements regarding identity and/or homology in the present application relate to the total length of the nucleic acid sequence or amino acid sequence given in each case.

In conjunction with the present disclosure, the statement that an amino acid position corresponds to a numerically designated position in SEQ ID NO:1 therefore means that the corresponding position of the numerically designated position in SEQ ID NO:1 is assigned in an alignment as defined above.

In another embodiment of the present disclosure, the amylase has a cleaning performance is not significantly reduced compared with that of an amylase that comprises an amino acid sequence that corresponds to the amino acid sequences given in SEQ ID NO:1, i.e. has at least about 70%, about 75%, about 80%, about 85%, about 90%, about 95% of the reference washing performance. The cleaning performance can be determined in a washing system that contains a washing agent in a dose of between from about 4.5 and about 7.0 grams per liter of washing liquor and contains the amylase, the amylases to be compared being used in the same concentration (based on the active protein) and the cleaning performance on a stain on cotton being determined by measuring the extent to which the washed textile has been cleaned. For example, the washing process may be carried out for about 60 minutes at a temperature of about 40° C. and the water may have a water hardness of between from about 5 and about 25°, preferably from about 10 and about 20°, more preferably from about 13 and about 17° and most preferably from about 15.5 and about 16.5° (German hardness). The concentration of the amylase in the washing agent specified for this washing system is from about 0.001 and about 1 wt. %, preferably from about 0.001 and about 0.1 wt. %, and more preferably from about 0.01 and about 0.005 wt. %, based on active, pure protein.

A preferred liquid washing agent for a washing system of this type has the following composition (all given in percentage by weight): about 7% alkylbenzene sulfonic acid, about 9% anionic surfactants, about 4% $C_{12}$-$C_{18}$ Na salts of fatty acids, about 7% non-ionic surfactants, about 0.7% phosphonates, about 3.2% citric acid, about 3.0% NaOH, about 0.04% anti-foam agents, about 5.7% 1,2-propanediol, about 0.1% preservatives, about 2% ethanol, about 0.2% dye transfer inhibitor, and the remainder demineralized water. Preferably, the dose of the liquid washing agent is between from about 4.5 and about 6.0 grams per liter of washing liquor, for example about 4.7, about 4.9 or about 5.9 grams per liter of washing liquor. Preferably, washing is carried out in a pH range of between from about pH 7.5 and about pH 10.5, preferably between from about pH 7.5 and about pH 9.

In the context of the present disclosure, the cleaning performance can be determined at about 40° C. using a liquid washing agent as stated above, the washing process preferably being carried out for about 60 minutes.

The whiteness, i.e. the whitening of stains, as a measure of the cleaning performance is determined using optical measurement methods, preferably photometrically. An apparatus suitable for this purpose is for example the CM508d Minolta spectrometer. Usually, the apparatuses used for the measurement are calibrated in advance with a white standard, preferably a supplied white standard.

The equal-activity use of the relevant amylase can ensure that, even if there is any divergence in the ratio of active substance to total protein (the values for the specific activity), the respective enzymatic properties, i.e. the cleaning performance on particular stains for example, are compared. Generally speaking, low specific activity can be compensated for by adding a greater quantity of protein. Furthermore, the enzymes to be examined can also be used in the same substance quantity or weight quantity if the enzymes to be examined have a different affinity for the test substrate in an activity test. In this context, the expression "same substance quantity" relates to the use of equal molar quantities of the enzymes to be examined. In this context, the expression "same weight quantity" relates to the use of equal weights of the enzymes to be examined.

The alpha-amylase activity is determined in a manner that is conventional in the art, specifically, preferably by an optical measurement method, preferably a photometric method. The test suitable for this purpose involves the alpha-amylase-dependent cleavage of the substrate para-nitrophenyl maltoheptaoside. The alpha-amylase cleaves this into para-nitrophenyl oligosaccharide. The para-nitrophenyl oligosaccharide is in turn catalyzed by the enzymes glucoamylase and alpha-glucosidase into glucose and para-nitrophenol. The presence of para-nitrophenol can be identified using a photometer, e.g. the Tecan Sunrise apparatus and the XFLUOR software, at about 405 nm, and thus allows a conclusion to be drawn on the enzymatic activity of the alpha-amylase.

The protein concentration can be determined by any known methods, for example the BCA method (bicinchoninic acid; 2,2'-biquinoline-4,4'-dicarboxylic acid) or the Biuret method (A. G. Gornall, C. S. Bardawill and M. M. David, J. Biol. Chem., 177 (1948), p. 751-766). In this regard, the active protein concentration can be determined by titration of the active centers by using a suitable irreversible inhibitor and determining the residual activity (cf. M. Bender et al., J. Am. Chem. Soc. 88, 24 (1966), p. 5890-5913).

By reacting with an antiserum or a particular antibody, proteins can be combined into groups of immunologically related proteins. The proteins belonging to such a group are exemplified by having the same antigenic determinants that are detected by an antibody. They are therefore structurally similar to one another such that they are detected by an antiserum or particular antibodies. The present disclosure therefore also relates to amylases that are exemplified in that they comprise at least one and more preferably two, three or four matching antigenic determinants with an amylase as contemplated herein. Owing to the fact that they match immunologically, amylases of this type are structurally similar to the amylases as contemplated herein such that they can also be assumed to have an identical function.

In comparison with the amylase described in SEQ ID NO:1, amylases as contemplated herein may have additional amino acid modifications, in particular amino acid substitutions, insertions or deletions. Amylases of this type are for example developed by targeted genetic modifications, i.e. by mutagenic methods, and are optimized for particular purposes or with respect to specific properties (for example with respect to their catalytic activity, stability, etc.). Furthermore, nucleic acids as contemplated herein can be introduced into recombination preparations and thus used to produce completely new amylases or other polypeptides.

The aim is to introduce targeted mutations such as substitutions, insertions or deletions into the known molecules in order to improve the cleaning performance of enzymes as contemplated herein, for example. To do this, in particular the surface charges and/or the isoelectric point of the molecules, and therefore their interactions with the substrate, can be modified. This means that for example the net charge of the enzymes can be modified in order to influence the substrate binding, in particular for use in washing and cleaning agents. Alternatively or additionally, one or more appropriate mutations can further increase the stability of the amylase and therefore improve its cleaning performance. Advantageous properties of individual mutations, e.g. individual substitutions, may be complementary. An amylase that has already been optimized with respect to certain properties, for example with respect to its activity and/or its tolerance in relation to the substrate spectrum, can therefore be additionally developed in the context of the present disclosure.

The following convention is used to describe substitutions that relate to precisely one amino acid position (amino acid exchanges): first, the naturally present amino acid is indicated in the form of the internationally accepted one-letter code, and is then followed by the associated sequence position and lastly the inserted amino acid. Multiple exchanges within the same polypeptide chain are separated from one another by slashes. For insertions, additional amino acids are stated after the sequence position. For deletions, the missing amino acid is replaced by a symbol, for example an asterisk or a dash, or an A is placed before the corresponding position. For example, N25Q describes the substitution of asparagine with glutamine in position 25, N25AQ describes the insertion of alanine after the amino acid asparagine in position 25 and N25* or AN25 describes the deletion of asparagine in position 25. This nomenclature is known to a person skilled in the field of enzyme technology.

The present disclosure therefore also relates to an amylase that can be obtained as a starter molecule from an amylase as described above by a single or multiple conservative amino acid substitutions. The term "conservative amino acid substitution" means the replacement (substitution) of an amino acid residue with another amino acid residue, said replacement not resulting in a modification of the polarity or charge in the position of the exchanged amino acid, e.g. the replacement of an apolar amino acid residue with another apolar amino acid residue. Conservative amino acid substitutions in the context of the present disclosure include for example: G=A=S, I=V=L=M, D=E, N=Q, K=R, Y=F, S=T, G=A=I=V=L=M=Y=F=W=P=S=T.

Alternatively or additionally, the amylase can be obtained from an amylase as contemplated herein as a starting molecule by fragmentation, deletion, insertion or substitution mutagenesis, and comprises an amino acid sequence which matches the starting molecule over a length of at least about 370, about 380, about 390, about 400, about 410, about 420, about 430, about 440, about 450, about 460, about 470, about 480, about 490, about 500, about 510, about 520, about 530 or about 536 interconnected amino acids.

It is possible, for example, to delete individual amino acids at the termini or in the loops of the enzyme without the endohydrolytic activity being lost or reduced as a result. In addition, the allergenicity of affected enzymes can for example also be lowered by fragmentation, deletion, insertion or substitution mutagenesis of this type, and therefore the usability of said enzymes is improved overall. Advantageously, the enzymes also retain their endohydrolytic activity after mutagenesis, i.e. their endohydrolytic activity corresponds at least to that of the starting enzyme, i.e. in the preferred embodiment, the endohydrolytic activity is at least about 80%, preferably at least about 90%, of the activity of the starting enzyme. Additional substitutions may also display advantageous effects. Both individual and several interconnected amino acids can be replaced with other amino acids.

In this case, the other amino acid positions are defined by an alignment of the amino acid sequence of an amylase as contemplated herein with the amino acid sequence of the amylase as given in SEQ ID NO:1. Furthermore, the assignment of the position is determined by the mature protein. This assignment can in particular also be used if the amino acid sequence of an amylase as contemplated herein has a higher number of amino acid residues than the amylase according to SEQ ID NO:1. Proceeding from the given positions in the amino acid sequence of the amylase, the modification positions in an amylase as contemplated herein are precisely those which are assigned to these positions in an alignment.

The correct assignment of the amino acids to be modified, i.e. in particular the functional equivalence thereof, can also be confirmed by comparative tests, according to which the two positions assigned to one another on the basis of an alignment are modified in the same way in both compared amylases, and it is observed whether the enzymatic activity is modified in the same way in the two. If, for example, an amino acid replacement in a particular position of the amylase according to SEQ ID NO:1 is accompanied by a modification to an enzymatic parameter, for example by an increase in the $K_M$ value, and if a corresponding modification to the enzymatic parameter, i.e. for example likewise an increase in the $K_M$ value, is observed in an amylase variant as contemplated herein, the amino acid replacement of which has been achieved by the same introduced amino acid, then this is considered to confirm the correct assignment.

All the above-mentioned substantive matter is also applicable to the method as contemplated herein for preparing an amylase. Accordingly, a method as contemplated herein further comprises one or more of the following method steps:

introducing single or multiple conservative amino acid substitutions in a starting amylase according to SEQ ID NO:1;
changing the amino acid sequence by fragmentation, deletion, insertion or substitution mutagenesis, such that the amylase comprises an amino acid sequence which matches the starting molecule over a length of at least about 370, about 380, about 390, about 400, about 410, about 420, about 430, about 440, about 450, about 460, about 470, about 480, about 490, about 500, about 510, about 520, about 530 or about 536 interconnected amino acids.

All the embodiments also apply to the methods as contemplated herein.

In additional embodiments of the present disclosure, the amylase or the amylase prepared using a method as contemplated herein is at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5%, about 98.8%, about 99.0%, about 99.2%, about 99.4%, about 99.6% or about 99.8% identical to the amino acid sequence given in SEQ ID NO:1 over the total length thereof.

The present disclosure also relates to an above-described amylase that is additionally stabilized, in particular by one or more mutations, for example substitutions, or by coupling to a polymer. This is because an increase in the stability during storage and/or during use, for example in the washing process, leads to the enzymatic activity lasting longer, and the cleaning performance therefore being improved. In principle, all the stabilization options that are described and/or expedient in the prior art may be considered. Stabilizations that are achieved by mutations of the enzyme itself are preferable since such stabilizations do not require any additional processing steps after the enzyme has been obtained. Examples of sequence modifications suitable for this purpose are set out above. Further suitable sequence modifications are known from the prior art.

Options for stabilization are, for example:
Protection against the effect of denaturing agents such as surfactants by mutations that bring about a modification to the amino acid sequence on the surface of the protein;
Replacing amino acids that are close to the N-terminus with those that presumably make contact with the remainder of the molecule by non-covalent interactions and thus contribute to maintaining the globular structure.

Preferred embodiments are those in which the enzyme is stabilized in several ways, since multiple stabilizing mutations have an additive or synergistic effect.

The present disclosure also relates to an amylase as described above, which has at least one chemical modification. An amylase having such a modification is referred to as a derivative, i.e. the amylase is derivatized.

In the context of the present application, derivatives are accordingly understood to mean those proteins of which the pure amino acid chain has been chemically modified. Such derivatizations may for example take place in vivo by the host cell that expresses the protein. In this regard, coupling low-molecular compounds such as lipids or oligosaccharides should be emphasized in particular. However, derivatizations may also be carried out in vitro, for example by the chemical conversion of a side chain of an amino acid or by covalent bonding of another compound to the protein. For example, it is possible to couple amines to carboxyl groups of an enzyme in order to modify the isoelectric point. Another compound of this type may also be another protein, which is for example bonded to a protein as contemplated herein by bifunctional chemical bonds. Derivatization is likewise understood to mean covalent bonding to a macromolecular carrier, or non-covalent inclusion in suitable macromolecular cage structures. Derivatizations may for example influence the substrate specificity or the bonding strength to the substrate, or may temporarily block the enzymatic activity if the coupled substance is an inhibitor. This may for example be useful during the storage period. Modifications of this type may also influence the stability or the enzymatic activity. They may also be used to reduce the allergenicity and/or immunogenicity of the protein and therefore to increase the skin compatibility thereof, for example. For example, coupling to macromolecular compounds, for example polyethylene glycol, can improve the protein in terms of stability and/or skin compatibility.

Derivatives of a protein as contemplated herein may also be understood to mean, in the broadest sense, preparations of these proteins. Depending on how it is obtained, reprocessed or prepared, a protein may be accompanied by various other substances, for example from the culture of the microorganisms produced. A protein may also have been mixed with other substances, for example in order to increase its storage stability. Therefore, all the preparations of a protein as contemplated herein are also as contemplated herein. This is also irrespective of whether or not this enzymatic activity actually occurs in a particular preparation. This is because it may be desirable for there to be little or no activity during storage, and for its enzymatic function to only begin when it is used. This may for example be controlled using appropriate accompanying substances. In particular, the common preparation of amylases together with specific inhibitors is possible in this regard.

Regarding all the above-described amylases and amylase variants and/or derivatives, in the context of the present disclosure those amylases of which the catalytic activity and/or substrate tolerance correspond to that of the amylase according to SEQ ID NO:1 are particularly preferred, the catalytic activity and substrate tolerance being determined as described above.

The present disclosure also relates to a nucleic acid that codes for an amylase as contemplated herein, and to a vector containing a nucleic acid of this type, in particular a cloning vector or an expression vector. In preferred embodiments, the nucleic acid is a nucleic acid according to SEQ ID NO:2.

Accordingly, a particularly preferred vector as contemplated herein is a vector that includes a nucleic acid according to SEQ ID NO:2.

In this case, this may relate to DNA or RNA molecules. They may be a single strand, a single strand that is complementary to this single strand, or a double strand. In DNA molecules in particular, the sequences of both complementary strands need to be taken into account in all three possible reading frames. In addition, it needs to be taken into account that various codons, i.e. base triplets, can code for the same amino acids, and therefore a particular amino acid sequence can be coded by several different nucleic acids. Owing to the genetic code being degenerated, all the nucleic acid sequences that can code for one of the above-described amylases are included in said subject matter of the present disclosure. A person skilled in the art is able to determine these nucleic acid sequences without any doubt, since, despite the genetic code being degenerated, defined amino acids can be assigned to individual codons. Therefore, proceeding from an amino acid sequence, a person skilled in the art can determine nucleic acids coding for this amino acid sequence without any problems. In addition, in nucleic acids as contemplated herein, one or more codons can be replaced with synonymous codons. This aspect relates in particular to the heterologous expression of the enzymes as contemplated herein. Therefore, each organism, for example a host cell of a production strain, has a particular codon use. "Codon use" is understood to mean the translation of the genetic code into amino acids by the organism in question. Bottlenecks in the protein biosynthesis may occur if the codons present on the nucleic acid in the organism are opposite a relative low number of loaded tRNA molecules. Although coding for the same amino acid, this means that a codon is less efficiently translated in the organism than a synonymous codon that codes for the same amino acid. Because there is a higher number of tRNA molecules for the synonymous codon, said codon can be more efficiently translated in this organism.

Using methods which are currently generally known, such as chemical synthesis or the polymerase chain reaction (PCR), in conjunction with molecular biological and/or protein chemical standard methods, it is possible for a person skilled in the art, on the basis of known DNA and/or amino acid sequences, to produce the corresponding nucleic acids and even complete genes. Methods of this type are known from Sambrook, J., Fritsch, E. F. and Maniatis, T. 2001. Molecular cloning: a laboratory manual, 3. Edition Cold Spring Laboratory Press.

In the context of the present disclosure, vectors are understood to mean elements which include nucleic acids and which contain a nucleic acid as contemplated herein as an exemplary nucleic acid range. Vectors allow establishment of this nucleic acid in a species or a cell line over multiple generations or cell divisions as a stable genetic element. Vectors are specific plasmids, i.e. circular genetic elements, in particular for use in bacteria. In the context of the present disclosure, a nucleic acid as contemplated herein is cloned into a vector. These may include vectors, for example, which originate from bacterial plasmids, from viruses, or from bacteriophages, or predominantly synthetic vectors or plasmids having elements of various origins. Using the further genetic elements which are present in each case, vectors are able to become established as stable units in the host cells in question over several generations. They may be present extrachromosomally as separate units or they may be integrated in a chromosome or chromosomal DNA.

Expression vectors include nucleic acid sequences that are capable of replicating in the host cells, preferably microorganisms, particularly preferably bacteria, that contain said sequences, and of expressing a contained nucleic acid here. The expression is in particular influenced by the promoter(s) that regulate(s) the transcription. In principle, the expression can take place due to the natural promoter which is originally localized in front of the nucleic acid to be expressed, but also both by a promoter of the host cell provided on the expression vector or by a modified or completely different promoter of another organism or host cell. In the present case, at least one promoter is available and used for the expression of a nucleic acid as contemplated herein. Expression vectors can also be regulated, for example by modifying the culturing conditions or when a certain cell density of the host cell containing said vectors is reached or by adding certain substances, in particular activators of gene expression. An example of such a substance is the galactose derivative isopropyl-β-D-thiogalactopyranoside (IPTG), which is used as an activator of the bacterial lactose operon (lac operon). By contrast with expression vectors, the contained nucleic acid is not expressed in cloning vectors.

The present disclosure also relates to a non-human host cell containing a nucleic acid as contemplated herein or a vector as contemplated herein, or containing an amylase as contemplated herein, in particular a non-human host cell which secretes the amylase into the medium surrounding the host cell. Preferably, a nucleic acid as contemplated herein or a vector as contemplated herein is transformed into a microorganism that then constitutes a host cell as contemplated herein. Alternatively, individual components, i.e. nucleic acid parts or fragments of a nucleic acid as contemplated herein, are introduced into a host cell such that the resulting host cell contains a nucleic acid as contemplated herein or a vector as contemplated herein. This approach is particularly suitable if the host cell already contains one or more components of a nucleic acid as contemplated herein or of a vector as contemplated herein and the additional components are then added accordingly. Methods for transforming cells are established in the prior art and are well known to a person skilled in the art. In principle, all cells, i.e. prokaryotic or eukaryotic cells, are suitable as host cells. Preferred host cells are those which may be advantageously managed genetically, which concerns, for example, transformation using the nucleic acid or the vector and stable establishment thereof, for example unicellular fungi or bacteria. In addition, preferred host cells are exemplified by good microbiological and biotechnological manageability. This relates, for example, to ease of culturing, high growth rates, low demands on fermentation media, and good production and secretion rates for foreign proteins. Preferred host cells as contemplated herein secrete the (transgenically) expressed protein into the medium surrounding the host cells. In addition, the amylases may be modified by the cells producing said amylases after they are prepared, for example by bonding sugar molecules, formylation, amination, etc. Post-translational modifications of this type can influence the function of the amylase.

Those host cells of which the activity can be regulated due to genetic regulation elements which are provided on the vector, for example, but which may also be present in these cells from the outset, represent additional preferred embodiments. These host cells may be induced to express, for example by the controlled addition of chemical compounds which are used as activators, by changing the culturing conditions, or upon reaching a certain cell density. This allows cost-effective production of the proteins as contemplated herein. One example of a compound as contemplated herein is IPTG, as described above.

Prokaryotic or bacterial cells are preferred host cells. Bacteria are exemplified by short generation times and lower demands on the culturing conditions. As a result, cost-effective culturing methods or preparation methods can be established. In addition, a person skilled in the art has a great wealth of experience with bacteria in fermentation technology. Gram-negative or gram-positive bacteria may be suitable for specific types of production for a wide range of reasons, such as nutrient sources, product formation rate, time required, etc., which can be identified using experiments in individual cases.

For gram-negative bacteria, such as *Escherichia coli*, numerous proteins are secreted into the periplasmatic space, i.e. the compartment between the two membranes which enclose the cells. This may be advantageous for particular applications. Furthermore, gram-negative bacteria may also be formulated such that they output the expressed proteins not only into the periplasmatic space, but also into the medium surrounding the bacterium. In contrast, gram-positive bacteria, for example *Bacilli* or *Actinomycetes* or other representatives of the Actinomycetales, have no outer membrane, so that secreted proteins are immediately delivered into the medium surrounding the bacteria, generally the culture medium, from which the expressed proteins may be purified. They can be directly isolated from the medium or can be processed further. In addition, gram-positive bacteria are related or identical to most source organisms for technically significant enzymes and usually form comparable enzymes themselves, and therefore they have similar codon use and their protein synthesis system is naturally organized accordingly.

Host cells as contemplated herein may be altered with regard to their requirements for the culture conditions, may have different or additional selection markers, or may also express different or additional proteins. These may also be host cells of the type that transgenically express several proteins or enzymes.

In principle, the present disclosure is applicable to all microorganisms, in particular to all fermentable microorganisms, and means that it is possible to prepare proteins as contemplated herein by using microorganisms of this type. Microorganisms of this type then constitute host cells within the meaning of the present disclosure.

In another embodiment of the present disclosure, the host cell is a bacterium, preferably one selected from the group of genera of *Escherichia, Klebsiella, Bacillus, Staphylococcus, Corynebacterium, Arthrobacter, Streptomyces, Stenotrophomonas* and *Pseudomonas*, more preferably one selected from the group of *Escherichia coli, Klebsiella planticola, Bacillus licheniformis, Bacillus lentus, Bacillus amyloliquefaciens, Bacillus subtilis, Bacillus alcalophilus, Bacillus globigii, Bacillus gibsonii, Bacillus clausii, Bacillus halodurans, Bacillus pumilus, Staphylococcus carnosus, Corynebacterium glutamicum, Arthrobacter oxidans, Streptomyces lividans, Streptomyces coelicolor* and *Stenotrophomonas maltophilia*.

The host cell may however also be a eukaryotic cell that has a cell nucleus. The present disclosure therefore also relates to a host cell that has a cell nucleus. By contrast with prokaryotic cells, eukaryotic cells are able to post-translationally modify the protein formed. Examples thereof are fungi such as *Actinomycetes* or yeasts such as *Saccharomyces* or *Kluyveromyces*. This may be particularly advantageous, for example, when, in the context of their synthesis, the proteins undergo specific modifications, which such systems allow. The modifications made by eukaryotic systems particularly in the context of protein synthesis include, for example, the binding of low-molecular compounds such as membrane anchors or oligosaccharides. Oligosaccharide modifications of this type may for example be desirable for reducing the allergenicity of an expressed protein. Coexpression with the enzymes naturally formed by cells of this type, such as cellulases, may be advantageous. In addition, thermophilic fungal expression systems may be particularly suited for the expression of temperature-resistant proteins or variants. In preferred embodiments of the present disclosure, the host cell is a *Basidiomycetes* cell. In more preferred embodiments, the host cell is a *Bacillus* cell.

The host cells as contemplated herein are cultured and fermented in the usual manner, for example in batch or continuous systems. In the first case, a suitable culture medium is inoculated with the host cells, and the product is harvested from the medium after a period of time that can be determined experimentally. Continuous fermentation is exemplified by the achievement of a steady state in which, over a comparatively long time period, cells die in part, but also regrow, and at the same time, the protein formed may be withdrawn from the medium.

Host cells as contemplated herein are preferably used to prepare amylases as contemplated herein. The present disclosure therefore also relates to a method for preparing an amylase, comprising
culturing a host cell as contemplated herein, and
isolating the amylase from the culture medium or from the host cell.

Said subject matter of the present disclosure preferably includes fermentation methods. Fermentation methods are known per se from the prior art, and represent the actual large-scale production step, which is generally followed by a suitable method for purifying the prepared product, for example the amylase as contemplated herein. All fermentation methods which are based on a corresponding method for preparing an amylase as contemplated herein represent embodiments of this subject matter of the present disclosure.

Fermentation methods which are exemplified in that the fermentation is carried out via an inflow strategy are considered in particular. In this regard, the media components that are consumed by the continuous culturing are fed. Significant increases both in the cell density and in the cell mass or dry mass, and/or in particular in the activity of the amylase of interest, may be achieved in this way. In addition, the fermentation may also be designed in such a way that undesirable metabolic products are filtered out, or neutralized by adding a buffer, or counterions which are appropriate in each case.

The prepared amylase may be harvested from the fermentation medium. A fermentation method of this type is preferred over isolation of the amylase from the host cell, i.e. a product preparation from the cell mass (dry mass), but requires suitable host cells or one or more suitable secretion markers or mechanisms and/or transport systems to be made available, so that the host cells secrete the amylase into the fermentation medium. Without secretion, the amylase can alternatively be isolated from the host cell, i.e. can be purified from the cell mass, for example by precipitation with ammonium sulfate or ethanol, or by chromatographic purification.

All of the substantive matter described above may be combined into methods for preparing amylases as contemplated herein.

The present disclosure also relates to an agent that contains an amylase as contemplated herein as described above. Preferably, the agent is a washing or cleaning agent.

This subject matter of the present disclosure includes all conceivable types of washing or cleaning agents, both concentrates and agents intended to be used undiluted, for use on a commercial scale, in washing machines or for hand washing or cleaning. These for example include washing agents for textiles, carpets, or natural fibers for which the name washing agent is used. These for example also include dishwashing detergents for dishwashers or manual dishwashing detergents or cleaners for hard surfaces such as metal, glass, porcelain, ceramic, tiling, stone, painted surfaces, plastics materials, wood, or leather for which the name cleaning agent is used, i.e. for example also scouring agents, glass cleaners, toilet rim blocks, etc. in addition to manual and automatic dishwashing detergents. In the context of the present disclosure, the washing and cleaning agents also include auxiliary washing agents, which are added to the actual washing agent when washing textiles manually or using a machine in order to achieve an additional effect. Furthermore, in the context of the present disclosure, washing and cleaning agents also include textile pre-treatment and post-treatment agents, i.e. agents with which the piece of laundry comes into contact before it is actually washed, for example in order to loosen stubborn dirt, and also those agents which give the laundry other desirable properties, such as a pleasant feel, reduced creases, or low static charge, in a step following the actual washing of the textiles. Amongst other things, softeners are also included in these last-mentioned agents.

The washing or cleaning agents as contemplated herein, which may be provided as powdered solids, in subsequently compressed particle form, as homogeneous solutions or as suspensions, may contain, in addition to an amylase as contemplated herein, all known ingredients that are standard in agents of this type, at least one additional ingredient preferably being provided in the agent. The agents as contemplated herein may in particular contain surfactants, builders, peroxygen compounds or bleach activators. Furthermore, they may contain water-miscible organic solvents, additional enzymes, sequestering agents, electrolytes, pH regulators and/or further auxiliaries such as optical brighteners, graying inhibitors, foam regulators, and dyes and fragrances, and combinations thereof.

In particular, a combination of an amylase as contemplated herein with one or more additional ingredient(s) of the agent is advantageous, since, in preferred embodiments as contemplated herein, an agent of this type has improved cleaning performance owing to resulting synergisms. A synergism of this type can be achieved in particular by the combination of an amylase as contemplated herein with a surfactant and/or a builder and/or a peroxygen compound or bleach activator.

Advantageous ingredients of agents as contemplated herein are disclosed in the international patent application WO 2009/121725, starting on page 5, penultimate paragraph, through to page 13, after the second paragraph. Reference is explicitly made to this disclosure, and the disclosure therein is incorporated in the present patent application.

An agent as contemplated herein advantageously contains the amylase in a quantity of from about 2 µg to about 20 mg, preferably from about 5 µg to about 17.5 mg, particularly preferably from about 20 µg to about 15 mg and most particularly preferably from about 50 µg to about 10 mg per g of the agent. Furthermore, the agent as contemplated herein can advantageously contain the amylase in a quantity of from about 0.00005 to about 15 wt. % based on the active enzyme, preferably of from about 0.0001 to about 5 wt. % and particularly preferably of from about 0.001 to about 1 wt. %. In addition, the amylase contained in the agent, and/or additional ingredients of the agent, are encased by a substance that is impermeable to the enzyme at room temperature or in the absence of water and is permeable to the enzyme under the conditions for using the agent. Such an embodiment of the present disclosure is thus exemplified in that the amylase in the washing or cleaning agent is encased by a substance that is impermeable to the enzyme at room temperature or in the absence of water. Furthermore, the washing or cleaning agent itself can also be packaged in a container, preferably an air-permeable container, from which it can be released shortly before use or during the washing process.

In other embodiments of the present disclosure, the agent is present in solid form, in particular as a flowable powder having a bulk density of from about 300 g/l to about 1200 g/l, in particular from about 500 g/l to about 900 g/l, or is present in pasty or liquid form, and/or
is present in gel form or pouch form, and/or
is present as a single-component system, or
is divided into a plurality of components.

These embodiments of the present disclosure include all the solid, powdered, liquid, gel-like or pasty delivery forms of agents as contemplated herein, which optionally may also include several phases and be present in compressed or non-compressed form. The agent may be present as a flowable powder, in particular having a bulk density of from about 300 g/l to about 1200 g/l, in particular from about 500 g/l to about 900 g/l, or from about 600 g/l to about 850 g/l. The solid delivery forms of the agent also include extrudates, granulates, tablets or pouches. Alternatively, the agent may also be liquid, gel-like or pasty, for example in the form of a non-aqueous liquid washing agent or a non-aqueous paste, or in the form of an aqueous liquid washing agent or a water-containing paste. Furthermore, the agent may be present as a single-component system. Agents of this type include one phase. Alternatively, an agent may also include several phases. An agent of this type is divided into a plurality of components.

Washing or cleaning agents as contemplated herein may exclusively contain an amylase. Alternatively, they may also contain other hydrolytic enzymes or other enzymes in a concentration that is expedient for the effectiveness of the agent. Agents that also include one or more additional enzymes thus constitute another embodiment of the present disclosure. All the enzymes that can bring about catalytic activity in the agent as contemplated herein, in particular protease, lipase, cellulase, hemicellulase, mannanase, tannase, xylanase, xanthanase, xyloglucanase, β-glucosidase, pectinase, carrageenase, perhydrolase, oxidase, oxidoreductase, or other amylases, which may differ from the amylases as contemplated herein, and mixtures thereof, can preferably be used as additional enzymes. Other enzymes are advantageously contained in the agent in a quantity of from about $1\times10^{-8}$ to about 5 percent by weight in each case, based on active protein. More preferably, each additional enzyme is contained in agents as contemplated herein in a quantity of from about $1\times10^{-7}$ to about 3 wt. %, from about 0.00001 to about 1 wt. %, from about 0.00005 to about 0.5 wt. %, from about 0.0001 to about 0.1 wt. % and particularly preferably from about 0.0001 to about 0.05 wt. %, based on active protein. Particularly preferably, the enzymes display synergistic cleaning performance against particular stains or soiling, i.e. the enzymes contained in the agent composition assist in the cleaning performance thereof. More particularly preferably, there is a synergism of this kind between the amylase as contemplated herein and another enzyme of an agent as contemplated herein, including in particular between said amylase and a lipase and/or a protease and/or a mannanase and/or a cellulase and/or a pectinase. Synergistic effects can occur not only between different enzymes, but also between one or more enzymes and additional ingredients of the agent as contemplated herein.

In the cleaning agents described herein, the enzymes to be used can also be prepared together with accompanying substances, for example from fermentation. In liquid formulations, the enzymes are preferably used as a liquid enzyme formulation/liquid enzyme formulations.

The enzymes are generally not made available in the form of the pure protein, but rather in the form of stabilized, storable and transportable preparations. These ready-made preparations include, for example, the solid preparations obtained through granulation, extrusion, or lyophilization or, particularly in the case of liquid or gel-like agents, solutions of the enzymes, advantageously maximally concentrated, low-moisture, and/or supplemented with stabilizers or other adjuvants.

Alternatively the enzymes can also be encapsulated, both for the solid and the liquid delivery form, for example through spray-drying or extrusion of the enzyme solution together with a preferably natural polymer or in the form of capsules, for example those in which the enzymes are enclosed in a set gel, or in those of the core-shell type in which an enzyme-containing core is coated with a water-impermeable, air-impermeable, and/or chemical-impermeable protective layer. In the case of overlaid layers, other active ingredients, such as stabilizers, emulsifiers, pigments, bleaching agents, or dyes, can be additionally applied. Such capsules are applied using inherently known methods, for example through shaking or roll granulation or in fluidized bed processes. Such granulates are advantageously low in dust, for example due to the application of polymeric film-formers, and stable in storage due to the coating.

The enzymes may also be placed inside water-soluble films. A film of this type allows the enzymes to be released upon contact with water. In the sense in which it is used here, "water-soluble" relates to a film structure that is preferably entirely water-soluble. However, films that are substantially water-soluble but have relatively low quantities of a material that is not water-soluble in the film structure, films containing materials that are only water-soluble at relatively high water temperatures or only under restricted pH conditions, and films that enclose a relatively thin layer of water-insoluble material are all covered by the term "water-soluble". Preferably, a film of this type includes (completely or partially hydrolyzed) polyvinyl alcohol (PVA). The film may, however, also contain, in addition to the PVA, acid/acrylate copolymers, preferably methacrylic acid/ethyl acrylate copolymer, as available from Beiland as GBC 2580 and 2600, styrene maleic anhydride copolymers (SMA) (available as Scripset (trade name) from Monsanto), ethylene and acrylic acid copolymers (EAA) or ethylene methacrylic acid copolymers (EMAA), known as an ionomer (available from DuPont), in which the acid content of EAA or EMAA is at least approximately 20 mol. %, polyether block amide copolymers, polyhydroxyvaleric acid (available as Biopol (trade name) resins from Imperial Chemical Industries), polyethylene oxide; water-soluble polyesters or copolyesters, polyethyloxazoline (PEOX 200 from Dow), and water-soluble polyurethane.

Moreover, it is possible to formulate two or more enzymes together, so that a single granulate has several enzyme activities.

The present disclosure also relates to a method for cleaning textiles or hard surfaces which is exemplified in that an agent as contemplated herein is used in at least one method step, or in that an amylase as contemplated herein becomes catalytically active in at least one method step, in particular such that the amylase is used in an amount of from about 40 µg to about 4 g, preferably from about 50 µg to about 3 g, particularly preferably from about 100 µg to about 2 g and more particularly preferably from about 200 µg to about 1 g.

In various embodiments, the above-described method is exemplified in that the amylase is used at a temperature of from about 0 to about 100° C., preferably from about 0 to about 60° C., more preferably from about 20 to about 45° C. and most preferably at about 40° C.

This includes both manual and automatic methods, with automatic methods being preferred. Methods for cleaning textiles are generally exemplified in that various cleaning-active substances are applied to the items to be cleaned in a plurality of method steps and are washed off again after the contact time, or in that the items to be cleaned are treated with a washing agent or a solution or dilution of this agent in another manner. The same applies to methods for cleaning all materials other than textiles, in particular hard surfaces. All conceivable washing or cleaning methods can be used in at least one of the method steps to enhance the application of a washing or cleaning agent as contemplated herein or of an amylase as contemplated herein, and therefore constitute embodiments of the present disclosure. All the substantive matter, subject matter and embodiments described for amylases as contemplated herein and agents containing said amylases are also applicable to the subject matter of the present disclosure. Therefore, at this point, reference is explicitly made to the disclosure at the appropriate point, with the indication that this disclosure also applies to the above methods as contemplated herein.

Since amylases as contemplated herein naturally already have hydrolytic activity and also exert this activity in media that otherwise does not have any cleaning power, such as in mere buffers, an individual and/or the only step of a method of this type may include an amylase as contemplated herein being brought into contact with the stain, preferably in a buffer solution or in water, as the only cleaning-active component if desired. This constitutes another embodiment of said subject matter of the present disclosure.

Alternative embodiments of said subject matter of the present disclosure are also constituted by methods for treating raw textile materials or for textile care in which an amylase as contemplated herein is active in at least one method step. Of these, methods for raw textile materials, fibers or textiles having natural components are preferred, and methods for textiles containing wool or silk are particularly preferred.

All the substantive matter, subject matter and embodiments described for amylases as contemplated herein and agents containing said amylases are also applicable to said subject matter of the present disclosure. Therefore, at this point, reference is explicitly made to the disclosure at the appropriate point, with the indication that this disclosure also applies to the above use as contemplated herein.

In another aspect, the present disclosure relates to the use of an amylase as contemplated herein or to an amylase obtained according to a method as contemplated herein in a washing or cleaning agent for removing starch-containing stains. All the substantive matter, subject matter and embodiments described for amylases as contemplated herein and agents containing said amylases are also applicable to said subject matter of the present disclosure.

EXAMPLES

Example 1

Brief Summary of the Experimental Procedure

Activity-based screening of a metagenomic database was carried out. In this case, the metagenomic database was compiled from a biogas reactor sample from Bremen. The "TOPO XL PCR Cloning Kit" (Invitrogen) was used to compile the metagenomic database. In this process, a wild-type enzyme according to SEQ ID NO:1, annotated as alpha-amylase, was discovered. The corresponding gene could be isolated, transformed into E. coli and then expressed therein. The amylase produced by E. coli demonstrates good washing performance on various starch-containing textiles.

The sequence is very different from the amylases used until now in L&HC. As a result, it provides many options for increasing the genetic diversity, and also of modifying the performance spectrum by mutagenesis if necessary.

Washing Agent Matrix Used

This is the washing agent matrix (commercially available, without enzymes, optical brighteners, perfume, and dyes) that was used for the washing test:

| Chemical name | wt. % active substance in the raw material | wt. % active substance in the formulation |
| --- | --- | --- |
| Water demineralized | 100 | Remainder |
| Alkyl benzene sulfonic acid | 96 | 4-7 |
| Anionic surfactants | 70 | 5-8 |
| $C_{12}$-$C_{18}$ fatty acid Na salt | 30 | 2-4 |
| Non-ionic surfactants | 100 | 4-7 |
| Phosphonates | 40 | 0.1-1 |
| Citric acid | 100 | 1-3 |
| NaOH | 50 | 0.1-1 |
| Defoamer | t.q. | 0.01-1 |
| Glycerin | 100 | 1-3 |
| Preservatives | 100 | 0.05-1 |
| Ethanol | 93 | 0.5-2 |

Without optical brighteners, perfume, dye and enzymes.
Dose: 4.7 g/l

Activity Assay

To determine the amylolytic activity of amylases as contemplated herein, a modified para-nitrophenyl maltoheptaoside was used, the terminal glucose unit of which was blocked by a benzylidene group. The amylase releases para-nitrophenyl oligosaccharide from this molecule, which in turn is converted into glucose and para-nitrophenol by the enzymes glucoamylase and alpha-glucosidase. Therefore, the quantity of the para-nitrophenol released is proportional to the activity of the amylase. The measurement is taken for example using the Quick-Start® test kit from Abbott (Abbott Park, Ill., USA). The increase in the absorption (405 nm) in the test preparation was identified at 37° C. for 3 minutes compared with a photometric control value (blank value). The calibration was carried out on the basis of an enzyme standard with known activity (e.g. Maxamyl®/Purastar® 2900 Genencor 2900 TAU/g). The analysis was carried out by determining the absorption difference dE (405 nm) per minute compared with the enzyme concentration of the standard.

Washing Test and Results

A washing test was carried out using the purified supernatant from *E. coli*, which contains the wild-type amylase as contemplated herein in SEQ ID NO:1.

Conditions: 40° C., 16° dH Water, 1 hour;
Enzyme concentration: 0.186 TAU/ml (determination of the amylase activity with benzylidene-blocked para-nitrophenyl maltoheptaoside); this corresponds to an amylase quantity that is used in washing agents as standard.
Stains:

| 1. C-S-26 | Corn starch |
| 2. C-S-27 | Potato starch |
| 3. C-S-28 | Rice starch |
| 4. C-S-29 | Tapioca starch |
| 5. Wfk 10062 | Starch/carbon |

Place punched-out fabric (diameter=10 mm) in microtiter plate, pre-heat washing liquor to 40° C., final concentration 4.7 g/l;
apply liquor and enzyme to the stain, incubate for 1 hour at 40° C. and 600 rpm;
then rinse the stain several times with clear water, let it dry and determine the brightness using a colorimeter.

The brighter the fabric, the better the cleaning performance. The L-value is measured here, which represents brightness, and the higher it is the better.

It is washed with a conventional liquid washing agent without enzymes.

Sample 1: Washing agent without amylase as a benchmark (comparative reference)

Sample 2: Washing agent plus amylase (as contemplated herein) Result (from CL 113):

| Stain | Sample 1 | Sample 2 |
|---|---|---|
| Corn starch | 76.1 | 86.8 |
| Potato starch | 75.1 | 86.7 |
| Rice starch | 75.8 | 85.1 |
| Tapioca starch | 75.6 | 87.0 |
| Starch/carbon black | 66.9 | 70.9 |

It is clear that the amylase as contemplated herein displays very good performance on all five stains. A significant improvement in performance is said to occur from 1 unit, and here an improvement of up to 11.3 units of improvement was achieved. As a negative control, the boiled, purified supernatant from the production organism *E. coli* that displays no washing performance (not shown) was washed as well (99° C. for 30 minutes).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An amylase comprising an amino acid sequence which has at least about 90% sequence identity to the amino acid sequence set forth in SEQ ID NO:1 over the total length thereof, wherein the amylase has enzymatic activity, wherein the amylase has a cleaning performance that is at least 90% of the cleaning performance of the amino acid sequence of SEQ ID NO: 1, wherein the cleaning performance is determined in a washing system that comprises a washing liquor and a washing agent in a dose of from about 4.5 and about 7.0 grams per liter of the washing liquor, wherein the washing agent comprises the amylase and the amylase to be compared in the same concentration, and wherein the cleaning performance is determined by measuring an extent to which a stain on cotton is cleaned after washing for about 60 minutes at a temperature of about 40° C. wherein the water has a hardness of from about 5 to about 25° German hardness, and wherein the concentration of the amylase in the washing agent is from about 0.001 and about 1 wt. % based on active, pure protein.

2. The amylase of claim 1 comprising an amino acid sequence which has at least about 98.8% sequence identity to the amino acid sequence given in SEQ ID NO: 1 over the total length thereof.

3. The amylase of claim 2 that is a free enzyme.

4. The amylase of claim 1, wherein the washing agent further comprises about 7 wt % alkylbenzene sulfonic acid, about 9 wt % anionic surfactants, about 4 wt % $C_{12}$-$C_{18}$ Na salts of fatty acids, about 7 wt % non-ionic surfactants, about 0.7 wt % phosphonates, about 3.2 wt % citric acid, about 3.0 wt % NaOH, about 0.04 wt % anti-foam agents, about 5.7 wt % 1,2-propanediol, about 0.1 wt % preservatives, about 2 wt % ethanol, about 0.2 wt % dye transfer inhibitor, and the remainder demineralized water and wherein washing is carried out at a pH of from about pH 7.5 to about pH 10.5.

5. The amylase of claim 1 comprising at least one matching antigenic determinant.

6. The amylase of claim 2 encoded by the nucleic acid set forth in SEQ ID NO: 2.

7. The amylase of claim 6, wherein the nucleic acid is contained in a cloning vector or an expression vector.

8. An amylase comprising an amino acid sequence which has at least about 90% sequence identity to the amino acid sequence set forth in SEQ ID NO:1 over the total length thereof, wherein the amylase has enzymatic activity, wherein the amylase has a cleaning performance that is at least 95% of the cleaning performance of the amino acid sequence of SEQ ID NO: 1, wherein the cleaning performance is determined in a washing system that comprises a washing liquor and a washing agent in a dose of from about 4.5 and about 7.0 grams per liter of the washing liquor, wherein the washing agent comprises the amylase and the amylase to be compared in the same concentration, and wherein the cleaning performance is determined by measuring an extent to which a stain on cotton is cleaned after washing for about 60 minutes at a temperature of about 40° C. wherein the water has a hardness of from about 5 to about 25° German hardness, and wherein the concentration of the amylase in the washing agent is from about 0.001 and about 1 wt. % based on active, pure protein.

9. The amylase of claim 8 that is a free enzyme.

10. The amylase of claim 8, wherein the washing agent further comprises about 7 wt % alkylbenzene sulfonic acid, about 9 wt % anionic surfactants, about 4 wt % $C_{12}$-$C_{18}$ Na salts of fatty acids, about 7 wt % non-ionic surfactants, about 0.7 wt % phosphonates, about 3.2 wt % citric acid, about 3.0 wt % NaOH, about 0.04 wt % anti-foam agents, about 5.7 wt % 1,2-propanediol, about 0.1 wt % preservatives, about 2 wt % ethanol, about 0.2 wt % dye transfer inhibitor, and the remainder demineralized water and wherein washing is carried out at a pH of from about pH 7.5 to about pH 9.

11. The amylase of claim 8 comprising at least four matching antigenic determinants.

12. The amylase of claim 8 encoded by the nucleic acid set forth in SEQ ID NO: 2.

13. The amylase of claim 12, wherein the nucleic acid is contained in a cloning vector or an expression vector.

* * * * *

SEQUENCE LISTING

```
<160> NUMBER OF SEQ ID NOS: 2

<210> SEQ ID NO 1
<211> LENGTH: 430
<212> TYPE: PRT
<213> ORGANISM: unknown
<220> FEATURE:
<223> OTHER INFORMATION: Amylase

<400> SEQUENCE: 1

Arg Arg Leu Arg Gln Lys His Trp Ile Arg Gly Ile Val Leu Leu Ile
1               5                   10                  15

Leu Thr Ser Leu Phe Leu Cys Ser Asn Leu Tyr Ala Gln Tyr Glu Gly
            20                  25                  30

Asn Gly Thr Asp Val Met Leu Gln Gly Phe His Trp Leu Ser Ala Asn
        35                  40                  45

Gly Asn Trp Trp Asn Thr Ile Ser Ala Asn Ala Ser Thr Ile Gln Ala
    50                  55                  60

Ala Gly Phe Thr Met Val Trp Phe Pro Pro Val Ser Leu Ser Val Ser
65                  70                  75                  80

Lys Glu Gly Tyr Leu Pro Thr Gln Trp Tyr Asn Leu Ser Ser Gln Tyr
                85                  90                  95

Gly Asn Gln Ser Ser Leu Gln Asn Ala Val Asn Ala Leu Lys Ser Arg
            100                 105                 110

Gly Ile Lys Pro Leu Ala Asp Ile Val Ile Asn His Arg Cys Gly Ser
        115                 120                 125

Thr Ser Trp Ala Asp Phe Thr Asn Ser Ser Phe Ala Asn Asn Asn Tyr
    130                 135                 140
```

```
Ala Ile Cys Ser Asn Asp Glu Tyr Phe Ala Pro Gly Asn Ser Gly Ala
145                 150                 155                 160

Gly Ile Ser Glu Arg Gly Ala Tyr Asp Thr Gly Glu Gly Tyr Ser Ala
            165                 170                 175

Gly Arg Asp Leu Asp His Thr Asn Thr Ser Val Gln Asn Glu Ile Lys
            180                 185                 190

Tyr Trp Leu Ser Trp Leu Lys Asn Thr Ile Gly Phe Gln Gly Trp Arg
            195                 200                 205

Tyr Asp Tyr Val Lys Gly Tyr Gly Ala Tyr Val Gly Met Tyr Asn
210                 215                 220

Thr Ala Thr Ser Pro Tyr Phe Ser Val Gly Glu Tyr Trp Pro Thr Asn
225                 230                 235                 240

Tyr Phe Asp Val Asn Asn Pro Asn Asn Trp Arg Gln Gln Ile Met Asn
            245                 250                 255

Trp Ile Asp Ala Thr Gly Gly Lys Ser Thr Ala Phe Asp Phe Val Thr
            260                 265                 270

Lys Pro Leu Leu Ala Glu Ala Phe Asn Asn Asn Ala Tyr Trp Arg Leu
            275                 280                 285

Arg Asp Ser Asp Gly Lys Pro Ala Gly Thr Ile Gly Trp Trp Pro Ala
290                 295                 300

Met Ser Val Thr Phe Leu Asp Asn His Asp Thr Gly Pro Ser Pro Gly
305                 310                 315                 320

Gly Gly Gln Asn His Trp Pro Phe Pro Ser Tyr His Val Ala Ala Gly
            325                 330                 335

Tyr Ala Tyr Ile Leu Thr His Pro Gly Ile Pro Cys Val Tyr Trp Pro
            340                 345                 350

His Tyr Phe Asp Trp Gly Ser Gly Leu Gln Asn Glu Ile Lys Asn Met
            355                 360                 365

Ile Ala Leu Arg Lys Ala Lys Gly Ile Lys Ser Thr Ser Thr Val Ser
            370                 375                 380

Ile Gln Val Ala Asp Ser Ser Lys Tyr Ala Ala Ile Ile Asp Gly Lys
385                 390                 395                 400

Val Ala Val Lys Ile Gly Pro Gly Ser Trp Ser Pro Ser Gly Ser Trp
            405                 410                 415

Asn Leu Ala Leu Ser Gly Asn Asn Tyr Ala Ile Trp Thr Lys
            420                 425                 430

<210> SEQ ID NO 2
<211> LENGTH: 1293
<212> TYPE: DNA
<213> ORGANISM: unknown
<220> FEATURE:
<223> OTHER INFORMATION: Amylase

<400> SEQUENCE: 2
agaaggttga gacagaagca ctggatccgt gggatagttc tccttattct cacaagtcta    60
tttttgtgca gtaacccttta tgcccagtat gagggaaatg gtactgacgt aatgctgcag   120
gggttccact ggctctcggc aaatggtaat tggtggaata ccatcagcgc caatgcctct   180
actattcaag ccgctggttt taccatggtc tggtttccgc cagtttcttt gtcggtcagt   240
aaagaagggt acctgcctac ccagtggtat aacctctcct cccaatacgg caatcaatca   300
agtttgcaga atgcagttaa tgctttaaag tcgcggggga ttaagcccct tgccgacatt   360
gttatcaatc accgttgcgg ttccactagc tgggcggatt ttaccaactc gtcctttgcc   420
```

```
aataataact acgcaatctg cagcaatgac gagtattttg cccccggtaa ctcgggcgcc      480
ggcatctccg agcggggcgc ctacgacact ggagaaggtt attctgccgg ccgtgacctg      540
gaccacacca atacttccgt tcaaaacgag ataaaatatt ggctgagttg gttgaaaaat      600
accattggtt tccaaggctg gcgttatgac tatgttaagg gatatggcgg cgcgtatgtc      660
ggcatgtata acaccgccac ctccccctac ttctcggtgg gtgagtattg gccgaccaac      720
tattttgacg tcaataaccc caacaattgg cggcagcaga ttatgaattg gatcgatgcc      780
accgggggta aatcaacggc ttttgacttt gtgaccaaac ctttattggc cgaggcgttc      840
aataacaatg cctattggcg cctgcgggat tctgatggca aacccgccgg gaccatcggt      900
tggtggccgg cgatgagcgt gacttttctg gataaccatg ataccggccc cagcccgggc      960
ggcgggcaaa accattggcc cttcccatcg taccatgtag ctgctggtta tgcttacatc     1020
ttaactcatc cgggtattcc gtgcgtttac tggcctcact acttcgactg gggcagcggc     1080
ttgcaaaatg agatcaaaaa catgattgcc ttgcggaaag ccaaaggcat taagagcacg     1140
tccactgtca gcattcaagt ggccgattcc tccaagtacg cggcaattat cgacggtaaa     1200
gtcgcagtca agattggccc gggcagctgg tcgccttccg gttcatggaa cctggctttg     1260
agcggcaata actatgccat ttggaccaag taa                                  1293
```